(12) United States Patent
Nakagaki et al.

(10) Patent No.: US 11,293,894 B2
(45) Date of Patent: Apr. 5, 2022

(54) GAS SENSOR AND METHOD OF PRODUCING GAS SENSOR

(71) Applicant: NGK INSULATORS, LTD., Aichi (JP)

(72) Inventors: Kunihiko Nakagaki, Nagoya (JP); Taku Okamoto, Nagoya (JP); Nobukazu Ikoma, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 366 days.

(21) Appl. No.: 16/438,530

(22) Filed: Jun. 12, 2019

(65) Prior Publication Data

US 2019/0383767 A1 Dec. 19, 2019

(30) Foreign Application Priority Data

Jun. 15, 2018 (JP) .............................. JP2018-114321

(51) Int. Cl.
*G01N 27/41* (2006.01)
*G01N 27/407* (2006.01)

(52) U.S. Cl.
CPC ......... *G01N 27/41* (2013.01); *G01N 27/4071* (2013.01); *G01N 27/4075* (2013.01)

(58) Field of Classification Search
None
See application file for complete search history.

(56) References Cited

U.S. PATENT DOCUMENTS

2004/0112765 A1* 6/2004 Alkemade ............ G01N 27/419
205/784
2019/0128833 A1 5/2019 Nakagaki

FOREIGN PATENT DOCUMENTS

WO 2017/222002 A1 12/2017

* cited by examiner

*Primary Examiner* — J. Christopher Ball
(74) *Attorney, Agent, or Firm* — Mattingly & Malur, PC (57) ABSTRACT

A gas sensor includes a structural body made up from a solid electrolyte that exhibits oxygen ion conductivity, a gas introduction port formed in the structural body, a preliminary chamber communicating with the gas introduction port and equipped with a preliminary pump electrode, a main chamber communicating with the preliminary chamber and equipped with a main pump electrode, and a measurement chamber communicating with the main chamber and equipped with a measurement electrode. In the gas sensor, at least a surface of the preliminary pump electrode is made of a material which exhibits a low activity with respect to a reaction between ammonia and oxygen.

7 Claims, 8 Drawing Sheets

GAS SENSOR AND METHOD OF PRODUCING GAS SENSOR

CROSS-REFERENCE TO RELATED APPLICATION

This application is based upon and claims the benefit of priority from Japanese Patent Application No. 2018-114321 filed on Jun. 15, 2018, the contents of which are incorporated herein by reference.

BACKGROUND OF THE INVENTION

Field of the Invention

The present invention relates to a gas sensor configured to detect the concentrations of gases within a gas to be measured, as well as to a method of producing such a gas sensor.

Description of the Related Art

Conventionally, gas sensors have been proposed which measure the concentrations of a plurality of target components such as NO (nitrogen oxide) and $NH_3$ (ammonia) and the like that coexist in the presence of oxygen, such as in an exhaust gas.

In International Publication No. WO 2017/222002, a gas sensor has been proposed, in which, in an oxygen ion conductive solid electrolyte, a preliminary chamber, a main chamber, an auxiliary chamber, and a measurement chamber which are partitioned by diffusion resistance members are provided, together with pumping electrodes being disposed in the respective chambers. With such a gas sensor, switching between progression and stoppage of an oxidation reaction of ammonia into nitrogen oxide taking place inside the preliminary chamber is performed by switching between driving and stopping of the pumping electrodes of the preliminary chamber. In addition, the gas concentrations of ammonia and nitrogen oxide are measured on the basis of a change in the pumping current of a measurement electrode, which occurs due to a difference in the diffusion rate of ammonia and nitrogen oxide from the auxiliary chamber into the main chamber.

SUMMARY OF THE INVENTION

Incidentally, the oxygen concentration in the exhaust gas fluctuates significantly depending on the operating conditions of the engine. In a situation in which the supply of fuel to the engine is constricted, the oxygen concentration in the exhaust gas may rise to a value that is close to the oxygen concentration within the atmosphere (20%).

However, with the gas sensor disclosed in International Publication No. WO 2017/222002, when the concentration of oxygen in the gas to be measured increases, it has been ascertained that a change in the pumping current of the measurement electrode does not appear, even if switching is carried out between driving or stopping of the pumping electrode of the preliminary chamber. Therefore, in such a conventional gas sensor, when the oxygen concentration in the gas to be measured becomes high, the gas concentrations of ammonia and nitrogen oxide cannot be segregated and separately measured.

The present invention has the object of providing a gas sensor and a method of producing such a gas sensor, which is capable of measuring the concentrations of a plurality of gas components in a gas to be measured, even in the case that the oxygen concentration in the gas to be measured is increased.

One aspect of the present invention is characterized by a gas sensor configured to measure the concentrations of a plurality of components in the presence of oxygen, including a structural body made up from a solid electrolyte that exhibits at least oxygen ion conductivity, a gas introduction port formed in the structural body and into which a gas to be measured is introduced, a preliminary chamber including a preliminary pump electrode and communicating with the gas introduction port, a main chamber including a main pump electrode and communicating with the preliminary chamber, an auxiliary chamber including an auxiliary pump electrode and communicating with the main chamber, a measurement chamber including a measurement electrode and communicating with the auxiliary chamber, a specified component measurement unit configured to measure a concentration of a specified component inside the measurement chamber, a preliminary oxygen concentration control unit configured to control the oxygen concentration inside the preliminary chamber based on a voltage of the preliminary pump electrode, a main oxygen concentration control unit configured to control the oxygen concentration inside the main chamber based on a voltage of the main pump electrode, and a target component acquisition unit configured to acquire concentrations of ammonia and nitrogen oxide, on the basis of a difference between a sensor output from the specified component measurement unit at a time of a first operation of the preliminary oxygen concentration control unit, and a sensor output from the specified component measurement unit at a time of a second operation of the preliminary oxygen concentration control unit, and one of the sensor outputs, wherein at least a surface of the preliminary pump electrode is made of a material which exhibits a low activity with respect to a reaction between ammonia and oxygen.

Another aspect of the present invention is a method for producing a gas sensor according to the aforementioned aspect, the method including a step of manufacturing the preliminary pump electrode by firing inside the preliminary chamber, together with the solid electrolyte that constitutes the above-described structural body, an Au (gold)/Pt (platinum) alloy containing 1 wt % or more of Au (gold) as a preparatory composition.

In accordance with the gas sensor and the method of producing the gas sensor according to the above-described aspects, even in the case that the concentration of oxygen in the gas to be measured is high, since a change in the pumping current at the measurement electrode appears in accordance with switching between driving and stopping of the pumping electrode of the preliminary chamber, it is possible to measure the concentrations of a plurality of gas components.

The above and other objects, features, and advantages of the present invention will become more apparent from the following description when taken in conjunction with the accompanying drawings, in which preferred embodiments of the present invention are shown by way of illustrative example.

DESCRIPTION OF THE PREFERRED EMBODIMENTS

A preferred embodiment of the present invention will be presented and described below with reference to the attached drawings. In the present specification, the term "to" when used to indicate a numerical range is used with the implication of including the numerical values written before and after the term as a lower limit value and an upper limit value of the numerical range.

First Embodiment

Figure 1:
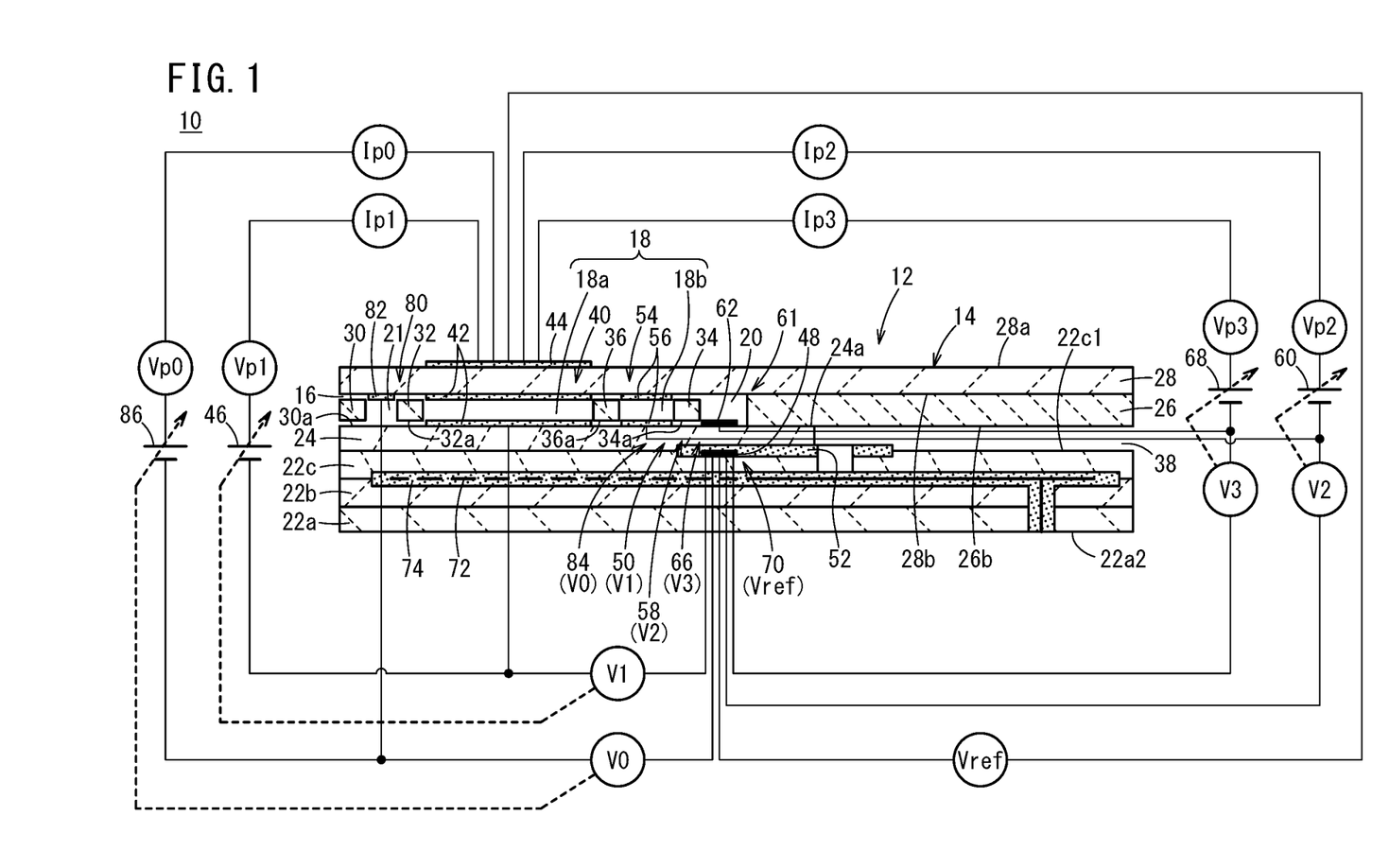
FIG. 1 is a cross-sectional view in which there is shown one structural example of a gas sensor according to an embodiment of the present invention.
Figure 2:
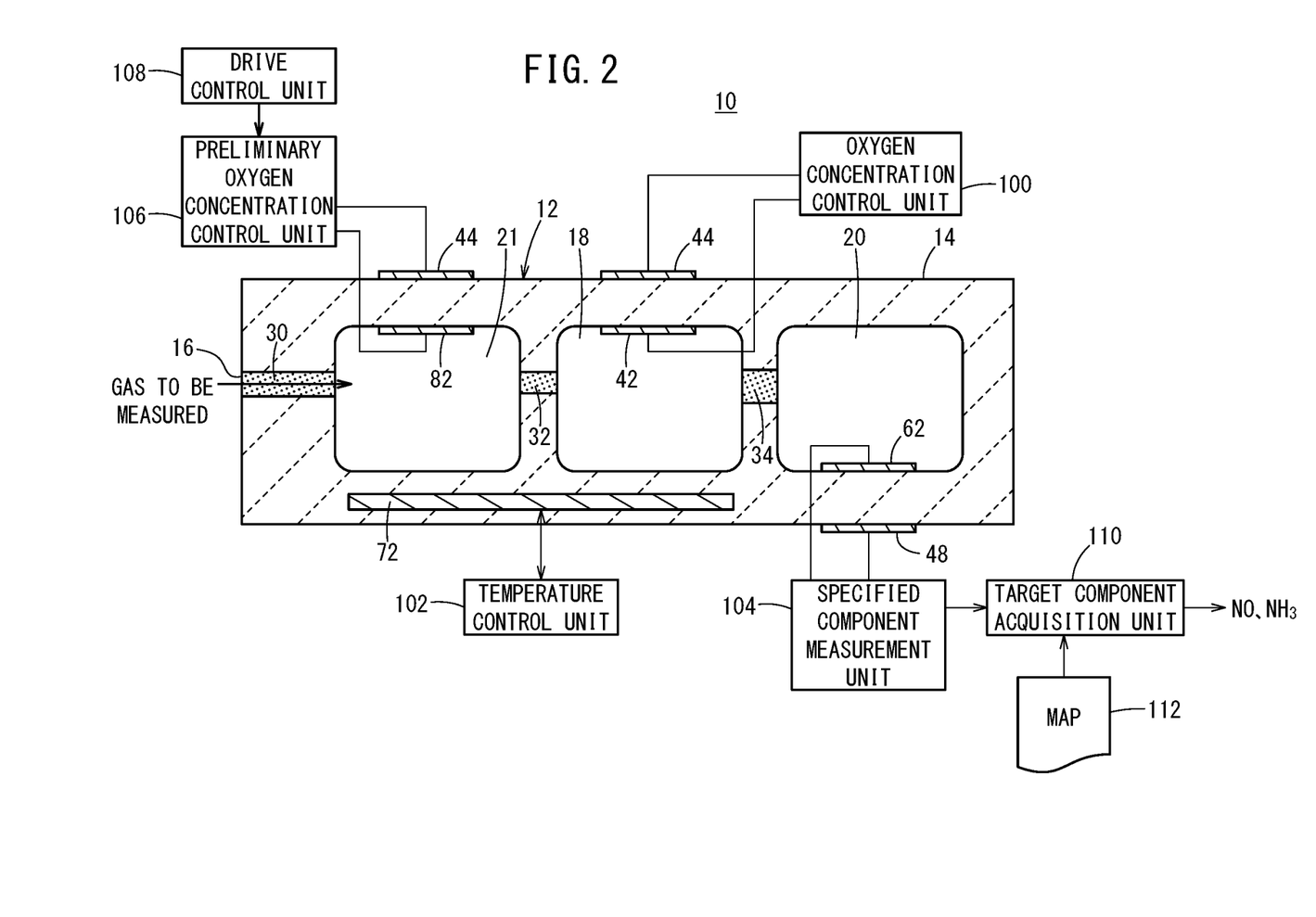
FIG. 2 is a configuration diagram schematically showing the gas sensor of FIG. 1.

As shown in FIGS. 1 and 2, a gas sensor 10 according to the present embodiment includes a sensor element 12. The sensor element 12 includes a structural body 14 made up from a solid electrolyte that exhibits at least oxygen ion conductivity, a gas introduction port 16 formed in the structural body 14 and into which a gas to be measured is introduced, an oxygen concentration adjustment chamber 18 formed in the structural body 14 and communicating with the gas introduction port 16, and a measurement chamber 20 formed in the structural body 14 and communicating with the oxygen concentration adjustment chamber 18.

The oxygen concentration adjustment chamber 18 includes a main chamber 18a disposed on the side of the gas introduction port 16, and an auxiliary chamber 18b communicating with the main chamber 18a. The measurement chamber 20 communicates with the auxiliary chamber 18b.

Furthermore, the gas sensor 10 includes a preliminary chamber 21 provided between the gas introduction port 16 and the main chamber 18a within the structural body 14. The main chamber 18a communicates with the gas introduction port 16 via the preliminary chamber 21.

The structural body 14 having such a plurality of chambers 18a, 18b, 20, and 21 is constituted by stacking a plurality of layers of substrates made from ceramics, for example. More specifically, the structural body 14 of the sensor element 12 is constituted by six layers made up from a first substrate 22a, a second substrate 22b, a third substrate 22c, a first solid electrolyte layer 24, a spacer layer 26, and a second solid electrolyte layer 28, which are stacked in this order from below. The layers are constituted, for example, from an oxygen ion conductive solid electrolyte such as zirconia ($ZrO_2$) or the like.

The gas introduction port 16 is provided at one end of the sensor element 12. The gas introduction port 16 is formed between a lower surface 28b of the second solid electrolyte layer 28 and an upper surface 24a of the first solid electrolyte layer 24.

Furthermore, between the lower surface 28b of the second solid electrolyte layer 28 and the upper surface 24a of the first solid electrolyte layer 24, there are formed a first diffusion rate control member 30, the preliminary chamber 21, a second diffusion rate control member 32, the oxygen concentration adjustment chamber 18, a third diffusion rate control member 34, and the measurement chamber 20. A fourth diffusion rate control member 36 is provided between the main chamber 18a and the auxiliary chamber 18b that make up the oxygen concentration adjustment chamber 18.

The gas introduction port 16, the first diffusion rate control member 30, the preliminary chamber 21, the second diffusion rate control member 32, the main chamber 18a, the fourth diffusion rate control member 36, the auxiliary chamber 18b, the third diffusion rate control member 34, and the measurement chamber 20 are formed adjacent to each other in a manner communicating in this order. The portion from the gas introduction port 16 leading to the measurement chamber 20 is also referred to as a gas flow section.

The gas introduction port 16, the preliminary chamber 21, the main chamber 18a, the auxiliary chamber 18b, and the measurement chamber 20 are formed so as to penetrate through the spacer layer 26 in the thickness direction. The lower surface 28b of the second solid electrolyte layer 28 is exposed on upper parts of these chambers 18a, 18b, 20, and 21, and the upper surface 24a of the first solid electrolyte layer 24 is exposed on lower parts thereof. Further, side parts of the chambers 18a, 18b, 20, and 21 are partitioned by the spacer layer 26 or the diffusion rate control members 30, 32, 34, and 36.

Any one of the first diffusion rate control member 30, the third diffusion rate control member 34, and the fourth diffusion rate control member 36 is provided as two horizontally elongated slits 30a, 34a, and 36a. More specifically, the slits 30a, 34a, and 36a include in upper and lower portions thereof slit-shaped openings which are elongated in a direction perpendicular to the surface of the drawing sheet. Further, the second diffusion rate control member 32 is provided as a single horizontally elongated slit 32a.

Further, a reference gas introduction space 38 is provided at the other end (an end opposite to the end where the gas introduction port 16 is provided) of the sensor element 12. The reference gas introduction space 38 is formed between an upper surface 22c1 of the third substrate 22c and a lower surface 26b of the spacer layer 26. Further, a side portion of the reference gas introduction space 38 is partitioned by a side surface of the first solid electrolyte layer 24. For example, oxygen or atmospheric air is introduced as a reference gas into the reference gas introduction space 38.

The gas introduction port 16 is a location that opens with respect to the external space, and the target gas to be measured is drawn into the sensor element 12 from the external space through the gas introduction port 16.

The first diffusion rate control member 30 is a location that imparts a predetermined diffusion resistance to the gas to be measured which is introduced from the gas introduction port 16 into the preliminary chamber 21. Details concerning the preliminary chamber 21 will be described later.

The second diffusion rate control member 32 is a location that imparts a predetermined diffusion resistance to the gas to be measured which is introduced from the preliminary chamber 21 into the main chamber 18a.

The main chamber 18a is provided as a space for the purpose of adjusting an oxygen partial pressure within the gas to be measured that is introduced from the gas introduction port 16. The oxygen partial pressure is adjusted by operation of a main pump cell 40.

The main pump cell 40 comprises an electrochemical pump cell, also referred to as a main electrochemical pumping cell, which is constituted by a main pump electrode 42, an exterior side pump electrode 44, and an oxygen ion conductive solid electrolyte which is sandwiched between the two pump electrodes. The main pump electrode 42 is provided substantially over the entire surfaces, respectively, of an upper surface 24a of the first solid electrolyte layer 24, a lower surface 28b of the second solid electrolyte layer 28, and side surfaces of the spacer layer 26 that define the main chamber 18a. The exterior side pump electrode 44 is formed on the upper surface 28a of the second solid electrolyte layer 28. The position of the exterior side pump electrode 44 is preferably disposed in a region corresponding to the main pump electrode 42 in a manner of being exposed to the external space. The main pump electrode 42 is preferably made of a material having a weakened reduction capability with respect to nitrogen oxide (NOx) components within the gas to be measured. For example, the main pump electrode can be configured as a rectangular porous cermet electrode as viewed in plan. More specifically, for example, a cermet electrode of $ZrO_2$ and a noble metal such as Pt (platinum) containing 0.1 to 30 wt % of Au (gold) can be used.

The main pump cell 40 applies a first pump voltage Vp1 supplied from a first variable power source 46 which is provided externally of the sensor element 12, and by allowing a first pump current Ip1 to flow between the exterior side pump electrode 44 and the main pump electrode 42, it is possible to pump oxygen in the interior of the main chamber 18a out to the exterior, or alternatively, to pump oxygen in the external space into the main chamber 18a.

Further, the sensor element 12 includes a first oxygen partial pressure detecting sensor cell 50 which is an electrochemical sensor cell. The first oxygen partial pressure detecting sensor cell 50 includes the main pump electrode 42, a reference electrode 48, and the oxygen ion conductive first solid electrolyte layer 24 sandwiched between these electrodes. The reference electrode 48 is an electrode formed between the first solid electrolyte layer 24 and the third substrate 22c, and is made of the same porous cermet as the exterior side pump electrode 44. The reference electrode 48 is formed with a rectangular shape as viewed in plan. Further, around the periphery of the reference electrode 48, a reference gas introduction layer 52 is provided, which is made from porous alumina and is connected to the reference gas introduction space 38. The reference gas in the reference gas introduction space 38 is introduced to the surface of the reference electrode 48 via the reference gas introduction layer 52. The first oxygen partial pressure detecting sensor cell 50 generates a first electromotive force V1 between the main pump electrode 42 and the reference electrode 48, which is caused by the difference in oxygen concentration between the atmosphere inside the main chamber 18a and the reference gas in the reference gas introduction space 38.

The first electromotive force V1 generated in the first oxygen partial pressure detecting sensor cell 50 changes depending on the oxygen partial pressure of the atmosphere existing in the main chamber 18a. In accordance with the aforementioned first electromotive force V1, the sensor element 12 feedback-controls the first variable power source 46 of the main pump cell 40. Consequently, the first pump voltage Vp1, which is applied by the first variable power source 46 to the main pump cell 40, can be controlled in accordance with the oxygen partial pressure of the atmosphere in the main chamber 18a.

The fourth diffusion rate control member 36 is a location that imparts a predetermined diffusion resistance to the gas to be measured, the oxygen concentration (oxygen partial pressure) of which is controlled by operation of the main pump cell 40 in the main chamber 18a, and guides the gas to be measured into the auxiliary chamber 18b.

The auxiliary chamber 18b is provided as a space for further carrying out adjustment of the oxygen partial pressure by an auxiliary pump cell 54, with respect to the gas to be measured which is introduced through the fourth diffusion rate control member 36, after the oxygen concentration (oxygen partial pressure) has been adjusted beforehand in the main chamber 18a. In accordance with this feature, the oxygen concentration inside the auxiliary chamber 18b can be kept constant highly accurately, and it is possible to measure the NOx concentration with high accuracy.

The auxiliary pump cell 54 is an electrochemical pump cell, and is constituted by an auxiliary pump electrode 56, which is provided substantially over the entirety of the lower surface 28b of the second solid electrolyte layer 28 facing toward the auxiliary chamber 18b, the exterior side pump electrode 44, and the second solid electrolyte layer 28. Moreover, in the same manner as the main pump electrode 42, the auxiliary pump electrode 56 is also formed using a material that weakens the reduction capability with respect to the NOx component within the gas to be measured.

The auxiliary pump cell 54, by applying a desired second pump voltage Vp2 between the auxiliary pump electrode 56 and the exterior side pump electrode 44, is capable of pumping out oxygen within the atmosphere inside the auxiliary chamber 18b into the external space, or alternatively, is capable of pumping in oxygen from the external space into the auxiliary chamber 18b.

Further, in order to control the oxygen partial pressure within the atmosphere inside the auxiliary chamber 18b, an electrochemical sensor cell is constituted by the auxiliary pump electrode 56, the reference electrode 48, the second solid electrolyte layer 28, the spacer layer 26, and the first solid electrolyte layer 24. More specifically, a second oxygen partial pressure detecting sensor cell 58 is constituted thereby for controlling the auxiliary pump.

The second oxygen partial pressure detecting sensor cell 58 generates a second electromotive force V2 between the auxiliary pump electrode 56 and the reference electrode 48, which is caused by a difference in the oxygen concentration between the atmosphere inside the auxiliary chamber 18b and the reference gas in the reference gas introduction space 38. The second electromotive force V2 generated in the second oxygen partial pressure detecting sensor cell 58 changes depending on the oxygen partial pressure of the atmosphere existing in the auxiliary chamber 18b.

Based on the aforementioned second electromotive force V2, the sensor element 12 carries out pumping of the auxiliary pump cell 54 by controlling the second variable power source 60. Consequently, the oxygen partial pressure within the atmosphere inside the auxiliary chamber 18b is controlled so as to become a low partial pressure that does not substantially influence the measurement of NOx.

Further, together therewith, a second pump current $Ip^2$ of the auxiliary pump cell 54 is used so as to control the second electromotive force V2 of the second oxygen partial pressure detecting sensor cell 58. More specifically, the second pump current Ip2 is input as a control signal to the second oxygen partial pressure detecting sensor cell 58. As a result, the second electromotive force V2 is controlled, and the gradient of the oxygen partial pressure within the gas to be measured, which is introduced into the auxiliary chamber 18b through the fourth diffusion rate control member 36, is controlled to remain constant at all times. When the gas sensor 10 is used as a NOx sensor, by the actions of the main pump cell 40 and the auxiliary pump cell 54, the oxygen concentration inside the auxiliary chamber 18b is maintained at a predetermined value with high accuracy for each of the conditions.

The third diffusion rate control member 34 is a location that imparts a predetermined diffusion resistance to the gas to be measured, the oxygen concentration (oxygen partial pressure) of which is controlled by operation of the auxiliary pump cell 54 in the auxiliary chamber 18b and guides the gas to be measured into the measurement chamber 20.

Measurement of the NOx concentration is primarily performed by operations of a measurement pump cell 61 provided in the measurement chamber 20. The measurement pump cell 61 is an electrochemical pump cell constituted by a measurement electrode 62, the exterior side pump electrode 44, the second solid electrolyte layer 28, the spacer layer 26, and the first solid electrolyte layer 24. The measurement electrode 62 is provided, for example, on the upper surface 24a of the first solid electrolyte layer 24 within the measurement chamber 20. The measurement electrode 62 is made of a material whose reduction capability with respect to the NOx component within the gas to be measured is higher than that of the main pump electrode 42. The measurement electrode 62 can be, for example, a porous cermet electrode. Further, for the measurement electrode 62, a material preferably is used that also functions as a NOx reduction catalyst for reducing NOx that exists within the atmosphere.

The measurement pump cell 61 generates oxygen by decomposing nitrogen oxide around the periphery of the measurement electrode 62 inside the measurement chamber 20. Furthermore, the measurement pump cell 61 is capable of pumping out the oxygen generated at the measurement electrode 62, and detecting the generated amount of oxygen as a measurement pump current Ip3, or stated otherwise, as a sensor output.

Further, in order to detect the oxygen partial pressure around the periphery of the measurement electrode 62 inside the measurement chamber 20, an electrochemical sensor cell, and more specifically, a third oxygen partial pressure detecting sensor cell 66 for controlling the measurement pump, is constituted by the first solid electrolyte layer 24, the measurement electrode 62, and the reference electrode 48. A third variable power source 68 is controlled based on a third electromotive force V3 detected by the third oxygen partial pressure detecting sensor cell 66.

The gas to be measured, which is introduced into the auxiliary chamber 18b, reaches the measurement electrode 62 inside the measurement chamber 20 through the third diffusion rate control member 34, under a condition in which the oxygen partial pressure is controlled. Nitrogen oxide existing within the gas to be measured around the periphery of the measurement electrode 62 is reduced to thereby generate oxygen. In this instance, the generated oxygen is subjected to pumping by the measurement pump cell 61. At this time, a third pump voltage Vp3 of the third variable power source 68 is controlled in a manner so that the third electromotive force V3 detected by the third oxygen partial pressure detecting sensor cell 66 becomes constant. The amount of oxygen generated around the periphery of the measurement electrode 62 is proportional to the concentration of nitrogen oxide within the gas to be measured. Accordingly, the nitrogen oxide concentration within the gas to be measured can be calculated using the measurement pump current Ip3 of the measurement pump cell 61. More specifically, the measurement pump cell 61 constitutes a specified component measurement unit 104 that measures the concentration of a specified component (NO) inside the measurement chamber 20.

Further, the gas sensor 10 includes an electrochemical sensor cell 70. The sensor cell 70 is constituted by the second solid electrolyte layer 28, the spacer layer 26, the first solid electrolyte layer 24, the third substrate 22c, the exterior side pump electrode 44, and the reference electrode 48. In accordance with the electromotive force Vref obtained by the sensor cell 70, it is possible to detect the oxygen partial pressure within the gas to be measured existing externally of the sensor.

Furthermore, in the sensor element 12, a heater 72 is formed in a manner of being sandwiched from above and below between the second substrate 22b and the third substrate 22c. The heater 72 generates heat by being supplied with power from the exterior through a non-illustrated heater electrode provided on a lower surface 22a2 of the first substrate 22a. As a result of the heat generated by the heater 72, the oxygen ion conductivity of the solid electrolyte that constitutes the sensor element 12 is enhanced. The heater 72 is embedded over the entire region of the preliminary chamber 21, the oxygen concentration adjustment chamber 18, and the measurement chamber 20, and a predetermined location of the sensor element 12 can be heated and maintained at a predetermined temperature. Moreover, a heater insulating layer 74 made of alumina or the like is formed above and below the heater 72, for the purpose of obtaining electrical insulation thereof from the second substrate 22b and the third substrate 22c. Hereinafter, the heater 72, the heater electrode, and the heater insulating layer 74 may also be referred to collectively as a heater portion.

In addition, the preliminary chamber 21 is driven by a later-described drive control unit 108 (see FIG. 2), and during driving thereof, functions as a space for adjusting the oxygen partial pressure within the gas to be measured which is introduced from the gas introduction port 16. The oxygen partial pressure is adjusted by operation of a preliminary pump cell 80.

The preliminary pump cell 80 is an electrochemical pump cell, which is constituted by a preliminary pump electrode 82 provided substantially over the entirety of the lower surface 28b of the second solid electrolyte layer 28 facing toward the preliminary chamber 21, the exterior side pump electrode 44, and the second solid electrolyte layer 28.

The preliminary pump cell 80, by applying a desired preliminary pump voltage Vp0 between the preliminary pump electrode 82 and the exterior side pump electrode 44, is capable of pumping out oxygen within the atmosphere inside the preliminary chamber 21 into the external space, or alternatively, is capable of pumping in oxygen from the external space into the preliminary chamber 21.

With the gas sensor 10 of the present embodiment, a material possessing a low activity toward the oxidation reaction of $NH_3$ into NO is used as the material constituting the preliminary pump electrode 82. More specifically, an Au (gold)/Pt (platinum) alloy mixed with Au (gold) is used as the material for the preliminary pump electrode 82. The concentration of Au (gold) is preferably 10 atm % or greater, at least at a location in the vicinity of the surface of the preliminary pump electrode 82. In this instance, the concentration of Au (gold) (atm %) is an atomic percentage determined by the number of Au atoms/(the number of Pt atoms+the number of Au atoms), and can be determined by X-ray photoelectron spectroscopy (XPS).

The above-described preliminary pump electrode 82 containing Au (gold) comprises a paste containing an Au/Pt alloy of a 1 to 5 wt % ratio amount of Au added to Pt that is coated beforehand in the preliminary chamber 21 when the first solid electrolyte layer 24, the spacer layer 26, and the second solid electrolyte layer 28 are stacked. Thereafter, the preliminary pump electrode 82 can be formed by being subjected to firing together with the zirconia that makes up the structural body 14, at a temperature, for example, on the order of 1400° C. By carrying out such a treatment, Au is deposited on the surface of the Au/Pt alloy particles, and a gold concentration of 10 to 60 atm % is achieved on the surface of the preliminary pump electrode 82.

The preliminary pump electrode 82 may be formed by methods other than the method described above. For example, the preliminary pump electrode 82 may be formed by forming an Au film on the surface of a Pt membrane by a plating method or a film forming method or the like.

Moreover the electrodes other than the preliminary pump electrode 82 preferably do not contain gold, or the concentration of gold therein is lower than the concentration of gold on the surface of the preliminary pump electrode 82. This is because, for example, when a high concentration of a material such as gold, which exhibits a low activity toward the oxidation reaction of $NH_3$ into NO, is contained on the surface of the main pump electrode 42 of the main chamber 18a, there is a concern that the oxidation reaction of $NH_3$ into NO will not proceed sufficiently in the main chamber 18a, leading to the occurrence of errors in measurement.

The gas sensor 10 includes a preliminary oxygen partial pressure detecting sensor cell 84 for controlling the preliminary pump, in order to control the oxygen partial pressure within the atmosphere inside the preliminary chamber 21. The preliminary oxygen partial pressure detecting sensor cell 84 includes the preliminary pump electrode 82, the reference electrode 48, the second solid electrolyte layer 28, the spacer layer 26, and the first solid electrolyte layer 24. The preliminary oxygen partial pressure detecting sensor cell 84 detects as a preliminary electromotive force V0 the electromotive force between the preliminary pump electrode 82 and the reference electrode 48, which is generated by a difference between the oxygen concentration within the atmosphere inside the preliminary chamber 21 and the oxygen concentration within the reference gas.

Moreover, the preliminary pump cell 80 carries out pumping by a preliminary variable power source 86, the voltage of which is controlled based on a preliminary electromotive force V0 detected by the preliminary oxygen partial pressure detecting sensor cell 84. Consequently, the oxygen partial pressure within the atmosphere inside the preliminary chamber 21 is controlled so as to become a low partial pressure that does not substantially influence the measurement of NOx.

Further, together therewith, a preliminary pump current Ip0 thereof is used so as to control the electromotive force of the preliminary oxygen partial pressure detecting sensor cell 84. More specifically, the preliminary pump current Ip0 is input as a control signal to the preliminary oxygen partial pressure detecting sensor cell 84, and by controlling the preliminary electromotive force V0, the gradient of the oxygen partial pressure within the gas to be measured, which is introduced from the first diffusion rate control member 30 into the preliminary chamber 21, is controlled so as to remain constant at all times.

The preliminary chamber 21 also functions as a buffer space. More specifically, it is possible to cancel fluctuations in the concentration of the gas to be measured, which occur due to pressure fluctuations of the gas to be measured in the external space. As such pressure fluctuations of the gas to be measured, there may be cited, for example, pulsations in the exhaust pressure of an automotive exhaust gas.

Furthermore, as shown schematically in FIG. 2, the gas sensor 10 includes an oxygen concentration control unit 100 (main oxygen concentration control unit) that controls the oxygen concentration inside the oxygen concentration adjustment chamber 18, a temperature control unit 102 that controls the temperature of the sensor element 12, the specified component measurement unit 104 that measures the concentration of a specified component (NO) inside the measurement chamber 20, a preliminary oxygen concentration control unit 106, a drive control unit 108, and a target component acquisition unit 110.

Moreover, the oxygen concentration control unit 100, the temperature control unit 102, the specified component measurement unit 104, the preliminary oxygen concentration control unit 106, the drive control unit 108, and the target component acquisition unit 110 are constituted by one or more electronic circuits having, for example, one or a plurality of CPUs (central processing units), memory devices, and the like. The electronic circuits are software-based functional units in which predetermined functions are realized, for example, by the CPUs executing programs stored in a storage device. Of course, the electronic circuits may be constituted by an integrated circuit such as an FPGA (Field-Programmable Gate Array), in which the plurality of electronic circuits are connected according to the functions thereof.

By being equipped with the preliminary chamber 21, the preliminary oxygen concentration control unit 106, the drive control unit 108, and the target component acquisition unit 110, in addition to the above-described oxygen concentration adjustment chamber 18, the oxygen concentration control unit 100, the temperature control unit 102, and the specified component measurement unit 104, the gas sensor 10 is made capable of acquiring the concentrations of NO (nitrogen oxide) and $NH_3$ (ammonia).

On the basis of the preset oxygen concentration condition, and the first electromotive force V1 generated in the first oxygen partial pressure detecting sensor cell 50 (see FIG. 1), the oxygen concentration control unit 100 feedback-controls the first variable power source 46, and adjusts the oxygen concentration inside the oxygen concentration adjustment chamber 18 to a concentration in accordance with the above-described condition.

The temperature control unit 102 feedback-controls the heater 72 on the basis of a preset sensor temperature condition, and the measured value from a temperature sensor (not shown) that measures the temperature of the sensor element 12, whereby the temperature of the sensor element 12 is adjusted to a temperature in accordance with the above-described condition.

By independent operation of the oxygen concentration control unit 100 or the temperature control unit 102, or alternatively, by cooperative operation of the oxygen concentration control unit 100 and the temperature control unit 102, the gas sensor 10 controls the state inside the oxygen concentration adjustment chamber 18, so as to convert all of the $NH_3$ into NO, without causing decomposition of NO inside the oxygen concentration adjustment chamber 18.

On the basis of the preset oxygen concentration condition, and the preliminary electromotive force V0 generated in the preliminary oxygen partial pressure detecting sensor cell 84 (see FIG. 1), the preliminary oxygen concentration control unit 106 feedback-controls the preliminary variable power source 86, thereby adjusting the oxygen concentration inside the preliminary chamber 21 to a concentration in accordance with the condition.

In addition, the target component acquisition unit 110 acquires the concentrations of NO and $NH_3$ on the basis of a difference between the sensor output from the specified component measurement unit 104 in accordance with a first operation of the preliminary oxygen concentration control unit 106, and the sensor output from the specified component measurement unit 104 in accordance with a second operation of the preliminary oxygen concentration control unit 106.

In this instance, NO and $NH_3$ in the gas to be measured are changed in the following manner, in accordance with a preliminary pump voltage Vp0 applied to the preliminary pump electrode 82 by the preliminary oxygen concentration control unit 106.

First, in a first voltage range, the $NH_3$ inside the preliminary chamber 21 is maintained in the form of $NH_3$. The $NH_3$ inside the preliminary chamber 21, while remaining in the form of $NH_3$, passes through the second diffusion rate control member 32 and arrives at the interior of the oxygen concentration adjustment chamber 18. Further, the NO inside the preliminary chamber 21, while remaining in the form of NO, passes through the second diffusion rate control member 32 and arrives at the interior of the oxygen concentration adjustment chamber 18.

In a second voltage range, the $NH_3$ inside the preliminary chamber 21 is oxidized into NO, passes through the second diffusion rate control member 32 and arrives at the oxygen concentration adjustment chamber 18. Further, the NO while remaining in the form of NO passes through the second diffusion rate control member 32 and arrives at the oxygen concentration adjustment chamber 18.

In a third voltage range, after the $NH_3$ inside the preliminary chamber 21 has been oxidized into NO, the NO is further decomposed into $N_2$ and $O_2$, which pass through the second diffusion rate control member 32 and arrive at the oxygen concentration adjustment chamber 18. Further, the NO inside the preliminary chamber 21 is decomposed into $N_2$ and $O_2$, which pass through the second diffusion rate control member 32 and arrive at the interior of the oxygen concentration adjustment chamber 18.

Assuming that a voltage applied to the preliminary pump electrode 82 when the preliminary oxygen concentration control unit 106 is stopped is given by Voff, a first voltage selected from within the first voltage range is given by Va, a second voltage selected from within the second voltage range is given by Vb, and a third voltage selected from within the third voltage range is given by Vc, the respective voltages described above obey one of the following relationships:

$$Va<Voff<Vb<Vc \text{ or } Voff<Va<Vb<Vc.$$

The preliminary oxygen concentration control unit 106 applies the first voltage Va as the preliminary pump voltage Vp0 at the time of the first operation, and outputs the second voltage Vb as the preliminary pump voltage Vp0 at the time of the second operation. Moreover, in accordance with the oxygen concentration of the gas to be measured, the oxygen may be pumped into the preliminary chamber 21, and in such a case, the first voltage Va may be of a negative value. In cases where oxygen is neither pumped out nor pumped into the preliminary chamber 21, the first voltage Va may be set to Voff.

As described above, at the time of the first operation, the $NH_3$ component passes in the form of $NH_3$ through the second diffusion rate control member 32, and is reflected in the measurement pump current (sensor output) Ip3. Further, at the time of the second operation, the $NH_3$ component passes as NO through the second diffusion rate control member 32, and is reflected in the measurement pump current (sensor output) Ip3. Since $NH_3$ is capable of being diffused through the second diffusion rate control member 32 more quickly than NO, the measurement pump current (sensor output) Ip3 undergoes a change between the time of the first operation and the time of the second operation. The magnitude of such differences reflects the concentration of $NH_3$ within the gas to be measured. More specifically, the measurement pump current (sensor output) Ip3 can be decomposed into an NO component and an $NH_3$ component using the difference in the diffusion rates of $NH_3$ and NO. Accordingly, the gas sensor 10 determines the concentrations of NO and $NH_3$ on the basis of a difference in the sensor output from the specified component measurement unit 104 in accordance with the second operation of the preliminary oxygen concentration control unit 106.

Next, processing operations of the gas sensor 10 will be described with reference also to FIGS. 3 and 4.

Figure 3:
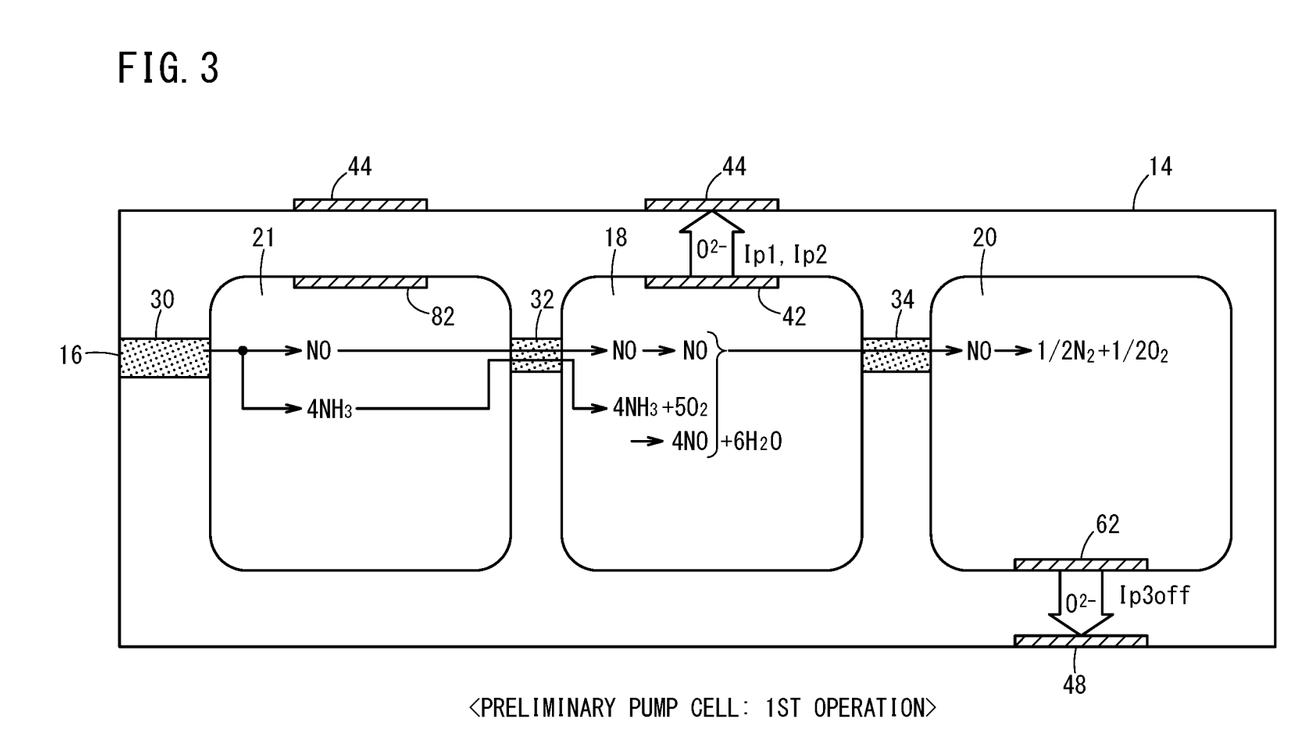
FIG. 3 is an explanatory diagram schematically showing reactions in a preliminary chamber, an oxygen concentration adjustment chamber, and a measurement chamber, for a case in which a preliminary pump cell is implementing a first operation.

First, as shown in FIG. 3, the $NH_3$ that was introduced through the gas introduction port 16 reaches the oxygen concentration adjustment chamber 18 during a period in which the preliminary oxygen concentration control unit 106 is implementing the first operation by the drive control unit 108. In the oxygen concentration adjustment chamber 18, by operation of the oxygen concentration control unit 100, a control is performed so as to convert all of the $NH_3$ into NO, and therefore, the $NH_3$ that has flowed into the oxygen concentration adjustment chamber 18 from the preliminary chamber 21 causes a reaction in which oxidation from $NH_3$ into NO takes place inside the oxygen concentration adjustment chamber 18, and all of the $NH_3$ inside the oxygen concentration adjustment chamber 18 is converted into NO. Accordingly, the $NH_3$ that was introduced through the gas introduction port 16 passes through the first diffusion rate control member 30 and the second diffusion rate control member 32 at the $NH_3$ diffusion coefficient (for example, 2.2 $cm^2/sec$), and after being converted into NO inside the oxygen concentration adjustment chamber 18, passes through the third diffusion rate control member 34 at the NO diffusion coefficient (for example, 1.8 $cm^2/sec$), and moves into the adjacent measurement chamber 20.

Figure 4:
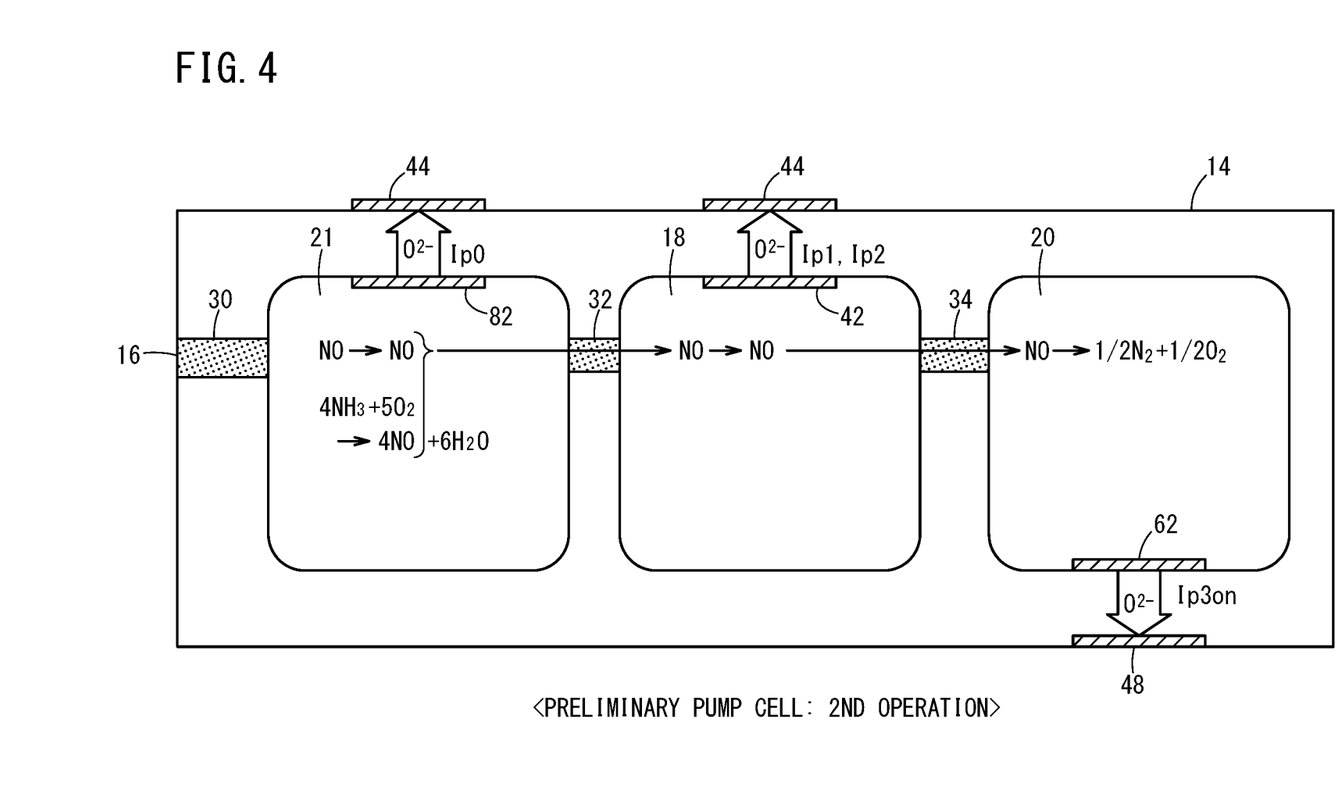
FIG. 4 is an explanatory diagram schematically showing reactions in a preliminary chamber, an oxygen concentration adjustment chamber, and a measurement chamber, for a case in which a preliminary pump cell is implementing a second operation.

On the other hand, during a period in which the preliminary oxygen concentration control unit 106 is implementing the second operation by the drive control unit 108, as shown in FIG. 4, the oxidation reaction from $NH_3$ into NO occurs inside the preliminary chamber 21, and all of the $NH_3$ that was introduced through the gas introduction port 16 is converted into NO. Accordingly, the $NH_3$ passes through the first diffusion rate control member 30 at the $NH_3$ diffusion coefficient, and thereafter the converted NO passes through the second diffusion rate control member 32 and the subsequent members, which lie beyond the preliminary chamber 21, at the NO diffusion coefficient, and moves into the measurement chamber 20.

Stated otherwise, by switching the preliminary oxygen concentration control unit 106 from the first operative state to the second operative state, the location where the oxidation reaction of $NH_3$ takes place is moved from the oxygen concentration adjustment chamber 18 to the preliminary chamber 21.

Changing of the location where the oxidation reaction of $NH_3$ takes place, from the oxygen concentration adjustment chamber 18 to the preliminary chamber 21 is equivalent to changing of a state of the $NH_3$ in the target gas when passing through the second diffusion rate control member 32, from $NH_3$ to NO. In addition, since NO and $NH_3$ possess different diffusion coefficients, the difference between passing through the second diffusion rate control member 32 with NO or passing therethrough with $NH_3$ is manifested as a difference in the amount of NO that flows into the measurement chamber 20, and thus the measurement pump current Ip3 that flows to the measurement pump cell 61 is made to change.

In this case, the measurement pump current Ip3(Vb) when the second operation of the preliminary pump cell 80 is performed, and the amount of change $\Delta$Ip3 in the measurement pump current Ip3(Va) at the time of the first operation of the preliminary pump cell 80 are uniquely determined by the concentration of $NH_3$ in the gas to be measured. Therefore, it is possible to calculate the concentrations of NO and $NH_3$ from the measurement pump current Ip3(Vb) or the measurement pump current Ip3(Va), and the amount of change $\Delta$Ip3 in the measurement pump current Ip3.

Accordingly, the target component acquisition unit 110 is capable of obtaining the concentrations of NO and $NH_3$ on the basis of a map 112 of the measurement pump current Ip3(Va) at the time of the first operation of the preliminary pump cell 80, and the amounts of change $\Delta$Ip3 in the measurement pump current Ip3 at the time of the first operation and at the time of the second operation.

Further, the target component acquisition unit 110 may obtain the $NH_3$ concentration on the basis of a correlation between the amount of change $\Delta$Ip3 and the $NH_3$ concentration which was determined in advance by experiment or simulation. In this case, the NO concentration can be obtained by subtracting the $NH_3$ concentration, which was obtained in the foregoing manner, from the NO concentration obtained from the sensor output at the time of the second operation of the preliminary pump cell 80, or in other words, the total NO concentration obtained by converting the total concentrations of NO and $NH_3$ into NO.

Exemplary Embodiments and Comparative Example

Hereinafter, advantageous effects of the preliminary pump electrode 82 containing Au (gold) will be described while referring to a comparative example and exemplary embodiments.

Comparative Example

The mechanical configuration of the gas sensor according to the comparative example is substantially the same as that of the gas sensor 10 according to the present embodiment. However, the comparative example differs from the gas sensor 10, in that the preliminary pump electrode 82 is made of only Pt and does not contain Au.

According to the comparative example, the first gas to be measured and the second gas to be measured having an oxygen concentration of 10% were supplied to the gas sensor, and the change in the measurement pump current Ip3 and the amount of change $\Delta$Ip3 thereof, with respect to the change in the preliminary pump voltage Vp0, were measured. Such a measurement was performed in a state with the gas sensor being maintained at 840° C. by the heater.

Moreover, the first gas to be measured is a gas having a temperature of 250° C., an $H_2O$ concentration of 3%, and an NO concentration of 500 ppm, and the flow rate thereof is 200 liters/min. In the following description, the first gas to be measured will be referred to as a "first gas to be measured (NO)".

Further, the second gas to be measured is a gas having a temperature of 250° C., an $H_2O$ concentration of 3%, and an $NH_3$ concentration of 500 ppm, and the flow rate thereof is 200 liters/min. In the following description, the second gas to be measured will be referred to as a "second gas to be measured ($NH_3$)".

Figure 5A:
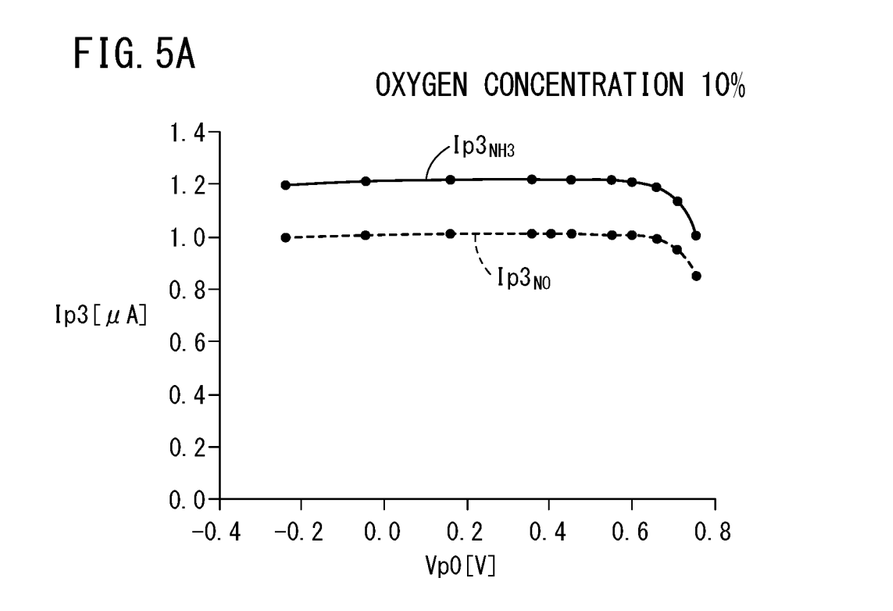
FIG. 5A is a graph showing measurement results of a measurement pump current Ip3 with respect to a preliminary pump voltage Vp0, in relation to a first gas to be measured (NO) and a second gas to be measured ($NH_3$), in a gas sensor according to a comparative example.

Measurement results of the measurement pump current $Ip3_{NO}$ with respect to the first measurement gas (NO), and measurement results of the measurement pump current $Ip3_{NH3}$ with respect to the second measurement gas ($NH_3$) are shown in FIG. 5A. Further, FIG. 5B shows the amount of change $\Delta$Ip3 obtained by subtracting the value of the measurement pump current Ip3, which gradually decreases accompanying an increase in the preliminary pump voltage Vp0, from the value of the measurement pump current Ip3 when Vp0 is −0.3 V.

Figure 5B:
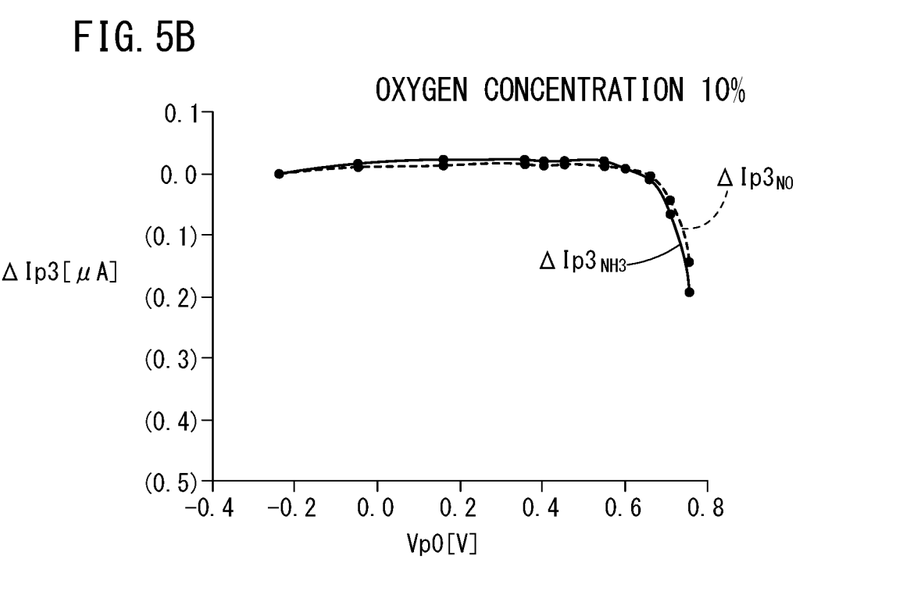
FIG. 5B is a graph showing an amount of change $\Delta$Ip3 in the measurement pump current Ip3 shown in FIG. 5A.

As shown in FIG. 5B, when attention is focused on $\Delta Ip3_{NO}$ and $\Delta Ip3_{NH3}$, there is almost no difference between them, and even if the preliminary pump voltage Vp0 is switched between a high voltage and a low voltage (or alternatively, Voff), no difference can be obtained between the values of $\Delta$Ip3 for the two types of gases $NH_3$ and NO. Such a feature is considered to occur because, in the case that the oxygen concentration is high, $NH_3$ becomes oxidized and changes into NO due to the catalytic activity of the electrode that is made from Pt in the preliminary chamber 21. Therefore, it is conjectured that, even in the event that the preliminary pump voltage Vp0 is set to a low voltage, $NH_3$ is changed into NO in the preliminary chamber 21, and a similar oxidation reaction takes place as when the preliminary pump voltage Vp0 is set to a high voltage. As a result, in the case that the oxygen concentration of the gas to be measured is as high as 10%, the concentrations of the two types of gases $NH_3$ and NO cannot be segregated or separately detected.

First Exemplary Embodiment

In the first exemplary embodiment, the preliminary pump electrode 82 of the gas sensor 10 was manufactured using a paste composed of an Au/Pt alloy containing 5 wt % of Au as a preparatory composition. The preliminary pump electrode 82 is formed by applying the Au/Pt alloy paste inside the preliminary chamber 21 when the structural body 14 is stacked or laminated to thereby form the preliminary chamber 21. Thereafter, the preliminary pump electrode 82 was formed by firing the applied Au/Pt alloy paste together with the structural body 14 at a temperature on the order of 1400° C.

When the gas sensor 10 of the first exemplary embodiment was cut, and the atomic percentage of the surface of the preliminary pump electrode 82 was measured by X-ray photoelectron spectroscopy (XPS), the atomic percentage of Au (gold) on the surface of the preliminary pump electrode 82 was determined to be 60 atm %.

Next, concerning the gas sensor 10 according to the first exemplary embodiment, the change in the measurement pump current (sensor output) Ip3 and the amount of change ΔIp3 of the measurement pump current Ip3, with respect to the preliminary pump voltage Vp0, were determined, when the first gas to be measured and the second gas to be measured having an oxygen concentration of 1% were supplied, as well as when the first gas to be measured and the second gas to be measured having an oxygen concentration of 10% were supplied thereto. The measurements by the gas sensor 10 were carried out in a state with the gas sensor 10 being maintained at 840° C. using the heater 72.

Moreover, the first gas to be measured (NO) is a gas having a temperature of 250° C., an $H_2O$ concentration of 3%, and an NO concentration of 500 ppm, and the flow rate thereof is 200 liters/min. Further, the second gas to be measured ($NH_3$) is a gas having a temperature of 250° C., an $H_2O$ concentration of 3%, and an $NH_3$ concentration of 500 ppm, and the flow rate thereof is 200 liters/min.

In the measurement of the first gas to be measured (NO), a change in the NO concentration for a case in which the preliminary pump voltage Vp0 was changed from −0.3 V to 0.8 V, i.e., a change in the measurement pump current (sensor output) $Ip3_{NO}$ in relation to NO, was determined. Further, a change in the amount of change $\Delta Ip3_{NO}$ obtained by subtracting the value of the measurement pump current $Ip3_{NO}$, which gradually decreases accompanying an increase in the preliminary pump voltage Vp0, from the value of the measurement pump current $Ip3_{NO}$ when the preliminary pump voltage Vp0 is −0.3 V was determined.

In the measurement of the second gas to be measured ($NH_3$), a change in the $NH_3$ concentration for a case in which the preliminary pump voltage Vp0 was changed from −0.3 V to 0.8 V, i.e., a change in the measurement pump current $Ip3_{NH3}$, was determined. Further, a change in the amount of change $\Delta Ip3_{NH3}$ obtained by subtracting the value of the measurement pump current $Ip3_{NH3}$, which gradually decreases accompanying an increase in the preliminary pump voltage Vp0, from the value of the measurement pump current $Ip3_{NH3}$ when the preliminary pump voltage Vp0 is −0.3 V was determined.

Figure 6A:
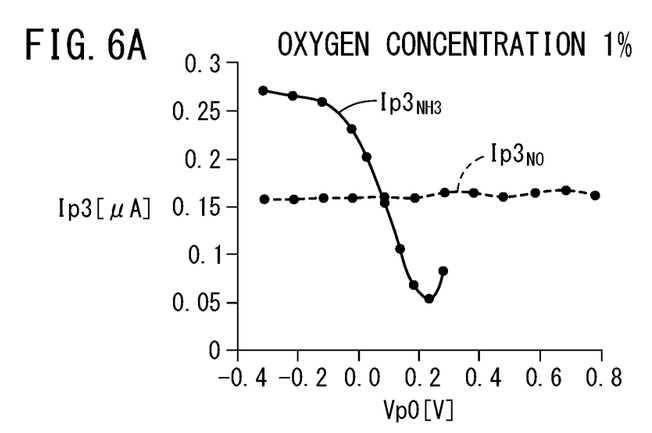
FIG. 6A is a graph showing a change in the measurement pump current Ip3 with respect to the preliminary pump voltage Vp0, in relation to the first gas to be measured (NO) and the second gas to be measured ($NH_3$), for which an oxygen concentration thereof is 1%, in a gas sensor according to a first exemplary embodiment.
Figure 6B:
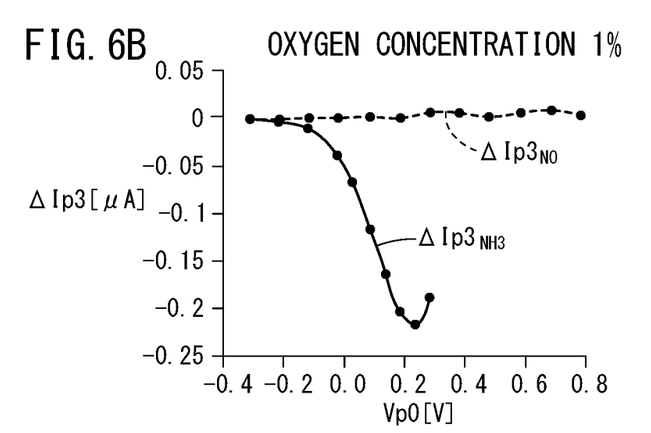
FIG. 6B is a graph showing an amount of change $\Delta$Ip3 in the measurement pump current Ip3 shown in FIG. 6A.

The measurement pump currents $Ip3_{NO}$ and $Ip3_{NH3}$ with respect to the first gas to be measured (NO) and the second gas to be measured ($NH_3$) when the oxygen concentration is 1% are shown in FIG. 6A, and the amounts of change $\Delta Ip3_{NO}$ and $\Delta Ip3_{NH3}$ thereof are shown in FIG. 6B. Further, the measurement pump currents $Ip3_{NO}$ and $Ip3_{NH3}$ with respect to the first gas to be measured (NO) and the second gas to be measured ($NH_3$) when the oxygen concentration is 10% are shown in FIG. 6C, and the amounts of change $\Delta Ip3_{NO}$ and $\Delta Ip3_{NH3}$ thereof are shown in FIG. 6D.

As shown in FIGS. 6A and 6B, the measurement pump current $Ip3_{NO}$ and the amount of change $\Delta Ip3_{NO}$ with respect to the first gas to be measured (NO) under the condition in which the oxygen concentration is 1% are of a constant value within a range in which the preliminary pump voltage Vp0 is −0.3 V to 0.8 V. From this fact, it can be understood that NO does not undergo decomposition at all, even if a comparatively high preliminary pump voltage Vp0 is applied.

On the other hand, the measurement pump current $Ip3_{NH3}$ and the amount of change $\Delta Ip3_{NH3}$ with respect to the second gas to be measured ($NH_3$) under the condition in which the oxygen concentration is 1% decrease sharply within a range in which the preliminary pump current Vp0 is 0 V to 0.2 V. Such a characteristic indicates that the oxidation reaction of $NH_3 \rightarrow NO$ takes place within the preliminary chamber 21 due to the rise in the preliminary voltage Vp0 to a value of greater than or equal to 0 V, and the $NH_3$ which is introduced through the gas introduction port 16 is converted into NO.

Figure 6C:
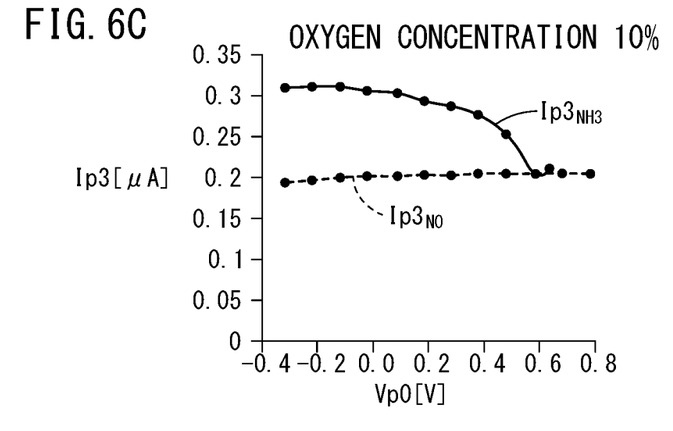
FIG. 6C is a graph showing a change in the measurement pump current Ip3 with respect to the preliminary pump voltage Vp0, in relation to the first gas to be measured (NO) and the second gas to be measured ($NH_3$), for which an oxygen concentration thereof is 10%.
Figure 6D:
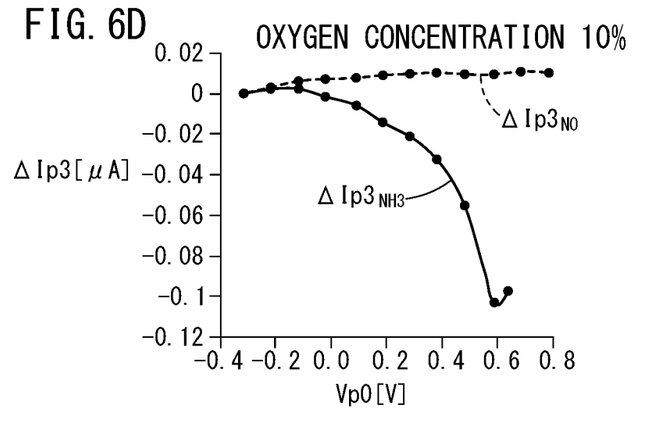
FIG. 6D is a graph showing an amount of change $\Delta$Ip3 in the measurement pump current Ip3 shown in FIG. 6C.

As shown in FIGS. 6C and 6D, under a condition in which the oxygen concentration is 10%, the measurement pump current $Ip3_{NO}$ and the amount of change $\Delta Ip3_{NO}$ with respect to the first gas to be measured (NO) are indicated as being of a constant value within a range in which the preliminary pump voltage Vp0 is −0.3 V to 0.8 V. From this fact, it can be understood that NO does not undergo decomposition, even if a comparatively high preliminary pump voltage Vp0 is applied.

Further, the measurement pump current $Ip3_{NH3}$ and the amount of change $\Delta Ip3_{NH3}$ with respect to the second gas to be measured ($NH_3$) under the condition in which the oxygen concentration is 10% undergo almost no change and are maintained at a constant value within a range in which the preliminary pump voltage Vp0 is −0.3 V to 0 V. Thus, according to the preliminary pump electrode 82 of the present embodiment, it can be understood that, even in the case that the oxygen concentration becomes as high as 10%, as long as the preliminary pump voltage Vp0 lies within the range of −0.3 V to 0 V, the reaction in which $NH_3$ is oxidized into NO does not occur.

Further, when the preliminary pump voltage Vp0 lies within a range of 0 V to 0.6 V, a result is shown in which the measurement pump current $Ip3_{NH3}$ and the amount of change $\Delta Ip3_{NH3}$ gradually decrease. Such a characteristic indicates that the oxidation reaction of $NH_3 \rightarrow NO$ takes place within the preliminary chamber 21 due to the rise in the preliminary voltage Vp0 to a value of greater than or equal to 0 V, and the $NH_3$ which is introduced through the gas introduction port 16 is converted into NO.

On the other hand, the measurement pump current $Ip3_{NO}$ and the amount of change $\Delta Ip3_{NO}$ with respect to the first gas to be measured (NO) under the condition in which the oxygen concentration is 10% are of a constant value within a range in which the preliminary pump voltage Vp0 is −0.3 V to 0.8 V. From this fact, it can be understood that NO does not undergo decomposition at all, even in the case that the oxygen concentration is 10%.

As can be appreciated from the above, even in the event that the oxygen concentration is high, by switching the preliminary pump voltage Vp0 between a high voltage and a low voltage (or alternatively, Voff), it is possible to obtain a difference in the values of the amount of change ΔIp3 for the two types of gases NH₃ and NO. Thus, according to the gas sensor of the first exemplary embodiment, even in the case that the oxygen concentration of the gas to be measured is high, it is possible to detect the concentrations of the two types of gases NH₃ and NO.

Incidentally, when attention is focused on the measurement pump current $Ip3_{NH3}$ and the measurement pump current $Ip3_{NO}$ shown in FIGS. 6A and 6B, the measurement pump current $Ip3_{NO}$ of the first gas to be measured (NO) remains constant regardless of the preliminary pump voltage Vp0. In contrast thereto, the measurement pump current $Ip3_{NH3}$ of the second gas to be measured (NH₃) becomes smaller corresponding to an increase in the preliminary pump voltage Vp0. If the operating mechanism of the gas sensor 10 as initially conceived is to increase the preliminary pump voltage Vp0, the reaction shown by the following chemical equation (1) should take place:

$$4NH_3 + 5O_2 \rightarrow 4NO + 6H_2O \qquad (1).$$

Accordingly, after the NH₃ has been converted into NO, the NO should not undergo any further decomposition, and should follow the same line as the measurement pump current $Ip3_{NO}$ of the first gas to be measured (NO).

However, contrary to the above expectation, the actually measured pump current $Ip3_{NH3}$ becomes smaller corresponding to an increase in the preliminary pump voltage Vp0. As a reason for this phenomenon, the inventors have considered that, on the preliminary pump electrode 82 which contains a high concentration of Au, due to the fact that the speed of the reaction is delayed, the reaction shown in FIG. 7 takes place. More specifically, in the preliminary pump electrode 82, a state in which NH₃ is abundant occurs about the periphery of the NO that is generated in the reaction of equation (1), and a reaction between NH₃ and NO takes place, as shown by the following chemical equation (2). As a result, it is considered that the amount of NH₃ (including NO after the reaction) in the second gas to be measured is reduced.

$$4NH_3 + 6NO \rightarrow 5N_2 + 6H_2O \qquad (2)$$

Figure 7:
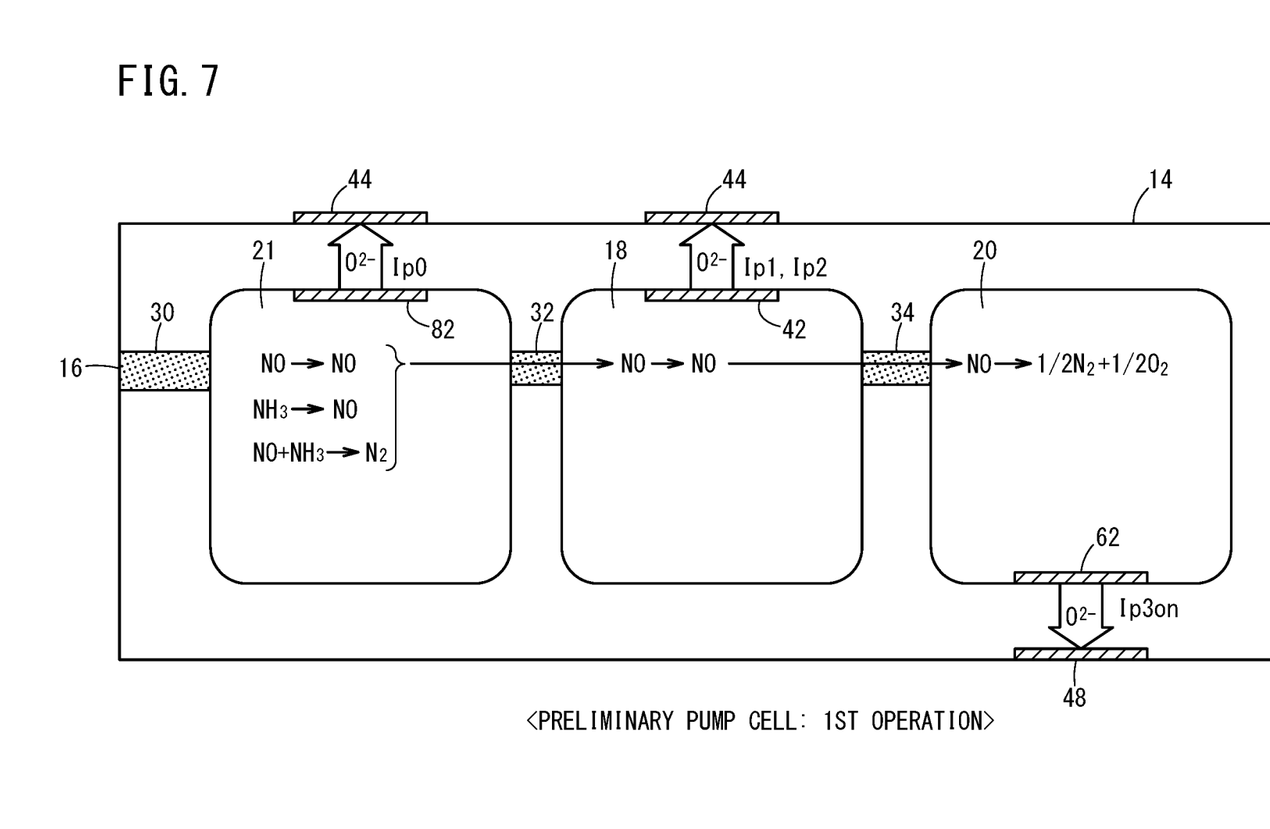
FIG. 7 is a schematic view showing a measurement mechanism of the gas sensor according to the first exemplary embodiment.

In this instance, in the case that NO and NH₃ are mixed within the atmosphere, the reaction of equation (2) takes place only if the gas to be measured enters into the preliminary chamber 21, and there is a concern that adequate sensitivity of the measurement pump current Ip3 cannot be obtained. Thus, when the inventors of the present invention conducted a test on a gas to be measured in which NO and NH₃ were actually mixed, the behavior of NO and NH₃ causing the reaction of equation (2) within the atmospheric gas could not be confirmed.

From this fact, the reaction of equation (2) does not seem to occur between NO and NH₃ which are introduced into the preliminary chamber 21 as gases to be measured, and it is considered that the reaction of equation (2) only occurs locally in the vicinity of the site where the reaction of equation (1) takes place on the surface of the preliminary pump electrode 82.

In the foregoing manner, in accordance with the preliminary pump electrode 82, which contains an atomic percentage of Au that is greater than or equal to 60 atm % as in the first exemplary embodiment, the change in the measurement pump current Ip3 when the preliminary pump voltage Vp0 is switched between a high voltage and a low voltage is manifested only by the NH₃ gas, and therefore, it becomes possible to segregate and separately detect the concentrations of NO and NH₃ in a wide region of oxygen concentrations.

Second Exemplary Embodiment

In the second exemplary embodiment, the preliminary pump electrode 82 of the gas sensor 10 was manufactured using a paste composed of an Au/Pt alloy containing 1 wt % of Au as a preparatory composition. The preliminary pump electrode 82 was formed by firing the applied Au/Pt alloy paste together with the structural body 14 at a temperature on the order of 1400° C. When the gas sensor 10 was cut, and the atomic percentage of the surface of the preliminary pump electrode 82 was measured by XPS, the atomic percentage of Au (gold) on the surface of the preliminary pump electrode 82 was determined to be 10 atm %.

Next, concerning the gas sensor 10 according to the second exemplary embodiment, the change in the measurement pump current (sensor output) Ip3 with respect to the preliminary pump voltage Vp0, and the amount of change ΔIp3 of the measurement pump current Ip3 were determined, when the first gas to be measured and the second gas to be measured having an oxygen concentration of 1% were supplied, as well as when the first gas to be measured and the second gas to be measured having an oxygen concentration of 10% were supplied thereto. The measurements by the gas sensor 10 of the present exemplary embodiment were carried out in a state with the gas sensor 10 being maintained at 840° C. using the heater 72.

In this instance, concerning the first gas to be measured (NO), the temperature thereof is 250° C., the H₂O concentration is 3%, the NO concentration is 500 ppm, and the flow rate thereof is 200 liters/min. Further, concerning the second gas to be measured (NH₃), the temperature thereof is 250° C., the H₂O concentration is 3%, the NH₃ concentration is 500 ppm, and the flow rate thereof is 200 liters/min.

In the measurement of the first gas to be measured (NO), a change in the NO concentration for a case in which the preliminary pump voltage Vp0 was changed from −0.3 V to 1.0 V, i.e., a change in the measurement pump current (sensor output) $Ip3_{NO}$ in relation to NO, was determined. Further, a change in the amount of change $\Delta Ip3_{NO}$ obtained by subtracting the value of the measurement pump current $Ip3_{NO}$, which gradually decreases accompanying an increase in the preliminary pump voltage Vp0, from the value of the measurement pump current $Ip3_{NO}$ when the preliminary pump voltage Vp0 is −0.3 V was determined.

In the measurement of the second gas to be measured (NH₃), a change in the NH₃ concentration for a case in which the preliminary pump voltage Vp0 was changed from −0.3 V to 1.0 V, i.e., a change in the measurement pump current $Ip3_{NH3}$, was determined. Further, a change in the amount of change $\Delta Ip3_{NH3}$ obtained by subtracting the value of the measurement pump current $Ip3_{NH3}$, which gradually decreases accompanying an increase in the preliminary pump voltage Vp0, from the value of the measurement pump current $Ip3_{NH3}$ when the preliminary pump voltage Vp0 is −0.3 V was determined.

Figure 8A:
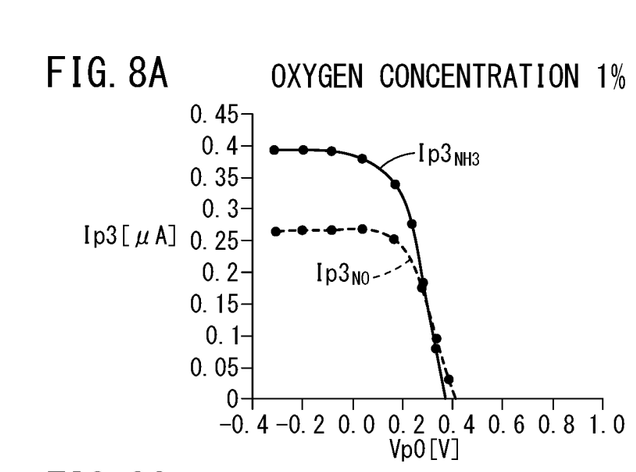
FIG. 8A is a graph showing a change in the measurement pump current Ip3 with respect to the preliminary pump voltage Vp0, in relation to the first gas to be measured (NO) and the second gas to be measured ($NH_3$), for which an oxygen concentration thereof is 1%, in a gas sensor according to a second exemplary embodiment.
Figure 8B:
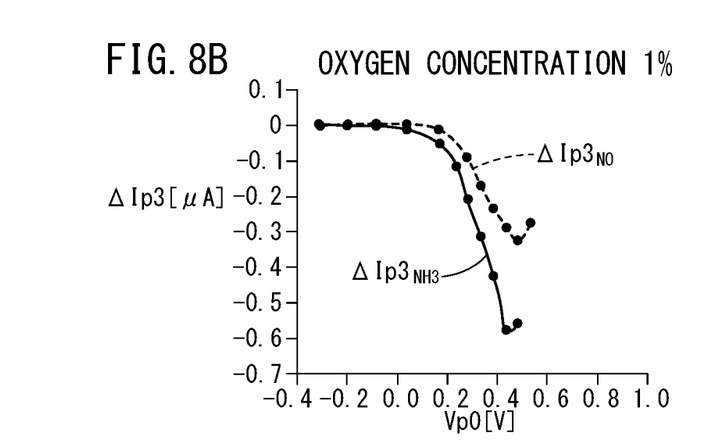
FIG. 8B is a graph showing an amount of change $\Delta$Ip3 in the measurement pump current Ip3 shown in FIG. 8A.

The measurement pump currents $Ip3_{NO}$ and $Ip3_{NH3}$ with respect to the first gas to be measured (NO) and the second gas to be measured (NH₃) when the oxygen concentration is 1% are shown in FIG. 8A, and the amounts of change $\Delta Ip3_{NO}$ and $\Delta Ip3_{NH3}$ thereof are shown in FIG. 8B. Further, the measurement pump currents $Ip3_{NO}$ and $Ip3_{NH3}$ with respect to the first gas to be measured (NO) and the second gas to be measured (NH₃) when the oxygen concentration is 10% are shown in FIG. 8C, and the amounts of change $\Delta Ip3_{NO}$ and $\Delta Ip3_{NH3}$ thereof are shown in FIG. 8D.

As shown in FIGS. 8A and 8B, the measurement pump current $Ip3_{NO}$ and the amount of change $\Delta Ip3_{NO}$ with respect to the first gas to be measured (NO) under the condition in which the oxygen concentration is 1% are of a constant value within a range in which the preliminary pump voltage Vp0 is −0.3 V to 0.1 V. Within such a range of the preliminary pump voltage Vp0, it is understood that NO does not undergo decomposition at all.

Further, the measurement pump current $Ip3_{NH3}$ and the amount of change $\Delta Ip3_{NH3}$ with respect to the second gas to be measured (NH$_3$) under the condition in which the oxygen concentration is 1% decrease sharply within a range in which the preliminary pump current Vp0 is 0.0 V to 0.1 V, which is a range in which the measurement pump current $Ip3_{NO}$ and the amount of change $\Delta Ip3_{NO}$ did not decrease. Such a characteristic indicates that the oxidation reaction of NH$_3$-j NO takes place within the preliminary chamber 21 due to the rise in the preliminary voltage Vp0 to a value of greater than or equal to 0.0 V, and the NH$_3$ which is introduced through the gas introduction port 16 is converted into NO.

Figure 8C:
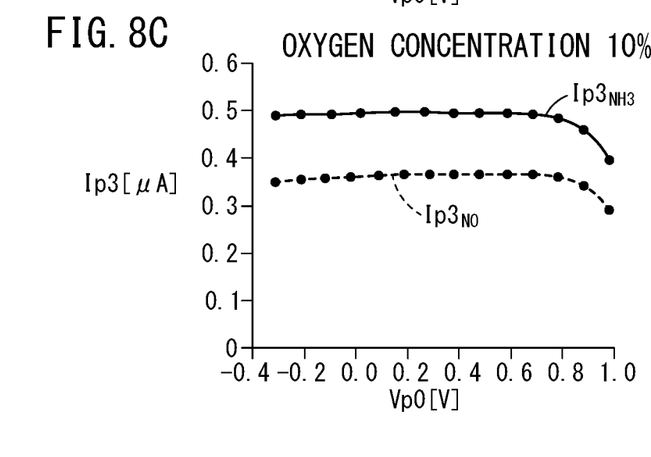
FIG. 8C is a graph showing a change in the measurement pump current Ip3 with respect to the preliminary pump voltage Vp0, in relation to the first gas to be measured (NO) and the second gas to be measured ($NH_3$), for which an oxygen concentration thereof is 10%.
Figure 8D:
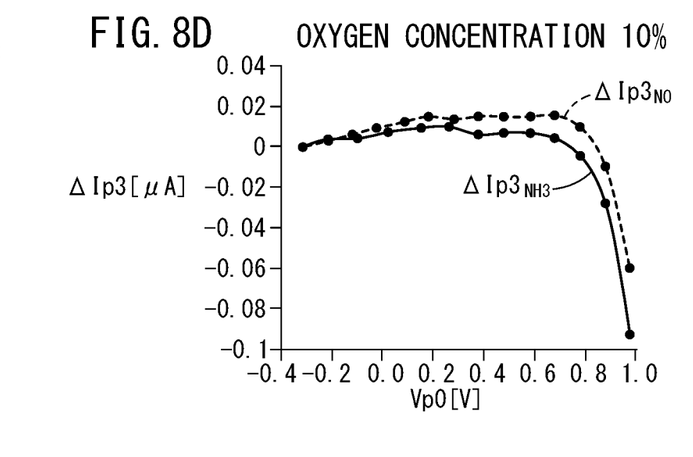
FIG. 8D is a graph showing an amount of change $\Delta$Ip3 in the measurement pump current Ip3 shown in FIG. 8C.

As shown in FIGS. 8C and 8D, the measurement pump current $Ip3_{NO}$ and the amount of change $\Delta Ip3_{NO}$ with respect to the first gas to be measured (NO) under the condition in which the oxygen concentration is 10% are of a constant value within a range in which the preliminary pump voltage Vp0 is −0.3 V to 0.8 V. From this fact, it can be understood that NO does not undergo decomposition at all, even if a comparatively high preliminary pump voltage Vp0 is applied.

Further, the measurement pump current $Ip3_{NH3}$ and the amount of change $\Delta Ip3_{NH3}$ with respect to the second gas to be measured (NH$_3$) under the condition in which the oxygen concentration is 10% undergo almost no change and are maintained at a constant value within a range in which the preliminary pump voltage Vp0 is −0.3 V to 0.2 V. Within this region, the amount of change $\Delta Ip3_{NH3}$ is substantially equal to the amount of change $\Delta Ip3_{NO}$. According to the preliminary pump electrode 82 of the present embodiment, it can be understood that, even in the case that the oxygen concentration becomes as high as 10%, the reaction in which NH$_3$ is oxidized into NO does not occur.

Further, when the preliminary pump voltage Vp0 lies within a range of 0.2 V to 0.9 V, a result is shown in which the measurement pump current $Ip3_{NH3}$ and the amount of change $\Delta Ip3_{NH3}$ decrease to values lower than when the preliminary pump voltage Vp0 lies within a range of −0.3 to 0.2V. Consequently, a difference occurs between the amount of change $\Delta Ip3_{NH3}$ and the amount of change $\Delta Ip3_{NO}$. Such a characteristic indicates that the oxidation reaction of NH$_3$→NO takes place within the preliminary chamber 21 due to the rise in the preliminary voltage Vp0 to a value of greater than or equal to 0.2 V, and the NH$_3$ which is introduced through the gas introduction port 16 is converted into NO. Although the difference between the amount of change $\Delta Ip3_{NH3}$ and the amount of change $\Delta Ip3_{NO}$ at this time is on the order of 0.01 µA, the magnitude of the difference can be sufficiently distinguished.

As can be appreciated from the above, even in the event that the oxygen concentration is high, by switching the preliminary pump voltage Vp0 between a high voltage and a low voltage, it is possible to obtain a difference in the values of the amount of change $\Delta Ip3$ for the two types of gases NH$_3$ and NO. Thus, according to the gas sensor 10 of the second exemplary embodiment, even in the case that the oxygen concentration of the gas to be measured is high, it is possible to detect the concentrations of the two types of gases NH$_3$ and NO.

The gas sensor 10 described above exhibits the following advantageous effects.

As shown in the first and second embodiments and the comparative example, in the gas sensor 10, by using the preliminary pump electrode 82 which is made from an Au/Pt alloy containing at least on a surface thereof an atomic percentage of Au that is greater than or equal to 10 atm %, oxidation of NH$_3$ inside the preliminary chamber 21 can be prevented. As a result, even in the case that the oxygen concentration within the gas to be measured becomes high, by switching the preliminary pump voltage Vp0 applied to the preliminary pump electrode 82 between a high voltage and a low voltage (or alternatively, Voff) and thereby utilizing the difference in the diffusion rates between NH$_3$ and NO in the second diffusion rate control member 32, the concentrations of these two types of gases can be segregated respectively and separately detected.

In the gas sensor 10, the concentration of Au (gold), which is a material that exhibits a low activity with respect to the reaction between ammonia and oxygen, on the surface of the preliminary pump electrode 82 is higher than the concentration of Au (gold) on the surface of the main pump electrode 42. In accordance with this feature, even in the case that the oxygen concentration within the gas to be measured is high, it is possible to prevent a reaction in which NH$_3$ is converted into NO inside the preliminary chamber 21, while on the other hand, it can be ensured that NH$_3$ can be converted into NO in the main chamber 18a.

In the gas sensor 10, by using an alloy containing Au (gold) which is a material that exhibits a low activity with respect to the reaction between ammonia and oxygen, a reaction in which NH$_3$ is converted into NO when the preliminary pump electrode 82 of the preliminary chamber 21 is at a low voltage can be prevented.

In the gas sensor 10, the concentration (atomic percentage) of Au (gold) on at least the surface of the preliminary pump electrode 82 is greater than or equal to 10 atm %. In accordance with this feature, when the preliminary pump voltage Vp0 of the preliminary pump electrode 82 is switched between a high voltage state and a low voltage state, changes in the outputs of the measurement pump current Ip3 and the amount of change $\Delta Ip3$ in accordance with the concentrations of NH$_3$ and NO can be detected. Consequently, it is possible for the concentrations of NH$_3$ and NO to be separately detected.

In the gas sensor 10, the preliminary pump electrode 82 may be made from an Au (gold)/Pt (platinum) alloy, and Au (gold) may be deposited or coated on the surface of the preliminary pump electrode 82. In this manner, the aforementioned effects can be obtained simply by increasing the concentration of Au (gold) on the surface of the preliminary pump electrode 82.

The preliminary pump electrode 82 of the gas sensor 10 according to the present embodiment can be obtained by firing inside the preliminary chamber 21, together with the solid electrolyte that constitutes the structural body 14, an Au (gold)/Pt (platinum) alloy containing 1 wt % or more of Au (gold) as a preparatory composition. In accordance with such a method, Au of high volatility and having a melting point which is lower than that of Pt diffuses and spreads within the preliminary chamber 21, and is deposited on the surface of the preliminary pump electrode 82. As a result, the preliminary pump electrode 82 having a high concentration of Au on the surface thereof is obtained.

Although the present invention has been described above by way of preferred embodiments, the present invention is not limited to the above-described embodiments, and it goes without saying that various modifications can be made within a range that does not depart from the essence and gist of the present invention.

What is claimed is:

1. A gas sensor configured to measure concentrations of a plurality of components in a presence of oxygen, comprising:
   a structural body made up from a solid electrolyte that exhibits at least oxygen ion conductivity;
   a gas introduction port formed in the structural body and into which a gas to be measured is introduced;
   a preliminary chamber including a preliminary pump electrode and communicating with the gas introduction port;
   a main chamber including a main pump electrode and communicating with the preliminary chamber;
   an auxiliary chamber including an auxiliary pump electrode and communicating with the main chamber;
   a measurement chamber including a measurement electrode and communicating with the auxiliary chamber;
   a measurement pump cell including the measurement electrode, the measurement pump cell pumping out oxygen generated at the measurement electrode and detecting the generated amount of oxygen as a sensor output that indicates a concentration of a specified component inside the measurement chamber;
   a preliminary pump cell including the preliminary pump electrode, the preliminary pump cell pumping out or pumping in oxygen to control an oxygen concentration inside the preliminary chamber based on a voltage of the preliminary pump electrode;
   a main pump cell including the main pump electrode, the main pump cell pumping out or pumping in oxygen to control the oxygen concentration inside the main chamber based on a voltage of the main pump electrode; and
   a processor coupled to a memory storing instructions that when executed by the processor configure the processor to:
   acquire concentrations of ammonia and nitrogen oxide, based on a difference between a first sensor output from the measurement pump cell at a time of a first operation of the preliminary pump cell, and a second sensor output from the measurement pump cell at a time of a second operation of the preliminary pump cell, and one of the first and second sensor outputs;
   wherein at least a surface of the preliminary pump electrode is made of a material which exhibits a low activity with respect to a reaction between ammonia and oxygen.

2. The gas sensor according to claim 1, wherein a concentration of the material on the surface of the preliminary pump electrode which exhibits a low activity with respect to the reaction between ammonia and oxygen is higher than a concentration of a material on a surface of the main pump electrode which exhibits a low activity with respect to the reaction between ammonia and oxygen.

3. The gas sensor according to claim 1, wherein the material which exhibits a low activity with respect to the reaction between ammonia and oxygen is an alloy containing Au (gold).

4. The gas sensor according to claim 1, wherein a concentration of Au (gold) on at least the surface of the preliminary pump electrode is greater than or equal to 10 atm %.

5. The gas sensor according to claim 4, wherein the preliminary pump electrode is made from an Au (gold)/Pt (platinum) alloy, and Au (gold) is deposited on the surface of the preliminary pump electrode.

6. The gas sensor according to claim 1, wherein the surface of the preliminary pump electrode is coated with a film containing Au (gold).

7. A method of producing a gas sensor, the gas sensor comprising:
   a structural body made up from a solid electrolyte that exhibits at least oxygen ion conductivity;
   a gas introduction port formed in the structural body and into which a gas to be measured is introduced;
   a preliminary chamber including a preliminary pump electrode and communicating with the gas introduction port;
   a main chamber including a main pump electrode and an exterior pump electrode, the main pump chamber communicating with the preliminary chamber;
   an auxiliary chamber including an auxiliary pump electrode and communicating with the main chamber;
   a measurement chamber including a measurement electrode and communicating with the auxiliary chamber;
   a measurement pump cell including the measurement electrode, the measurement pump cell pumping out oxygen generated at the measurement electrode and detecting the generated amount of oxygen as a sensor output that indicates a concentration of a specified component inside the measurement chamber;
   a preliminary pump cell including the preliminary pump electrode, the preliminary pump cell pumping out or pumping in oxygen to control an oxygen concentration inside the preliminary chamber based on a voltage of the preliminary pump electrode;
   a main pump cell including the main pump electrode, the main pump cell pumping out or pumping in oxygen to control the oxygen concentration inside the main chamber based on a voltage of the main pump electrode; and
   a processor coupled to a memory storing instructions that when executed by the processor configure the processor to:
   acquire concentrations of ammonia and nitrogen oxide, based on a difference between a first sensor output from the measurement pump cell at a time of a first operation of the preliminary pump cell, and a second sensor output from the measurement pump cell at a time of a second operation of the preliminary pump cell, and one of the first and second sensor outputs,
   wherein the method of producing the gas sensor includes a step of manufacturing the preliminary pump electrode by firing inside the preliminary chamber, together with the solid electrolyte that constitutes the structural body, an Au (gold)/Pt (platinum) alloy containing 1 wt % or more of Au (gold) as a preparatory composition.

* * * * *